US011911274B2

(12) United States Patent
Park (10) Patent No.: US 11,911,274 B2
(45) Date of Patent: Feb. 27, 2024

(54) ARTIFICIAL HEART VALVES INCORPORATING NEGATIVE POISSON'S RATIO MATERIALS

(71) Applicant: Joon Bu Park, Huntington Beach, CA (US)

(72) Inventor: Joon Bu Park, Huntington Beach, CA (US)

(*) Notice: Subject to any disclaimer, the term of this patent is extended or adjusted under 35 U.S.C. 154(b) by 126 days.

(21) Appl. No.: 17/512,340

(22) Filed: Oct. 27, 2021

(65) Prior Publication Data
US 2023/0126111 A1    Apr. 27, 2023

(51) Int. Cl.
*A61F 2/24*    (2006.01)

(52) U.S. Cl.
CPC .......... *A61F 2/2454* (2013.01); *A61F 2/2415* (2013.01)

(58) Field of Classification Search
CPC .... A61F 2/2454; A61F 2/2515; A61F 2/2403; A61F 2210/00; A61F 2210/0057; A61F 2210/0066; A61F 2210/0076; A61F 2220/0091; A61F 2250/0026; A61F 2250/0029
See application file for complete search history.

(56) References Cited

U.S. PATENT DOCUMENTS

| | | | | |
|---|---|---|---|---|
| 5,554,186 | A | * | 9/1996 | Guo ....................... A61F 2/2403 623/2.28 |
| 7,632,309 | B1 | | 12/2009 | Brendzel et al. |
| 10,314,700 | B2 | | 6/2019 | Sogard et al. |
| 2005/0089205 | A1 | * | 4/2005 | Kapur .................... A61B 8/483 382/128 |
| 2011/0319991 | A1 | * | 12/2011 | Hariton .................. E03C 1/025 623/2.14 |
| 2017/0007400 | A1 | | 1/2017 | Sogard et al. |
| 2018/0193137 | A1 | | 7/2018 | Gründeman et al. |
| 2019/0103600 | A1 | * | 4/2019 | Greer ................. H01M 4/8626 |
| 2019/0374229 | A1 | | 12/2019 | Anderson et al. |
| 2023/0048709 | A1 | * | 2/2023 | Park ........................ F16L 11/12 |
| 2023/0058045 | A1 | * | 2/2023 | Park ...................... A61L 31/086 |

OTHER PUBLICATIONS

Coulter et al., "Bioinspired Heart Valve Prosthesis Made by Silicone Additive Manufacturing," Elsevier Inc., Matter 1, Jul. 10, 2019, 1(1):266-279.
International Search Report and Written Opinion in International Appln. No. PCT/US 2022147748, dated May 23, 2023, 10 pages.
Paluck, et al., "Heparin-Mimicking Polymers: Synthesis and Biological Applications," Bio Macromolecules, Oct. 14, 2016, 17(11): 3417-3440.

* cited by examiner

*Primary Examiner* — Paul B Prebilic
(74) *Attorney, Agent, or Firm* — Fish & Richardson P.C.

(57) ABSTRACT

An artificial heart valve includes a frame, one or more struts attached to the frame, and a leaflet configured to open and close a fluid flow path through the frame by moving in response to heartbeats. Movement of the leaflet is restricted by the one or more struts. The leaflet includes an inner leaflet body having a negative Poisson's ratio, and an outer leaflet body at least partially surrounding the inner leaflet body, the outer leaflet body having a positive Poisson's ratio.

15 Claims, 9 Drawing Sheets

+ Foaming Agent

Heat/Pressure

Aperture formation

Heat/Pressure

ARTIFICIAL HEART VALVES INCORPORATING NEGATIVE POISSON'S RATIO MATERIALS

BACKGROUND

The present disclosure relates generally to materials for and construction of artificial heart valves, for example, artificial heart valve leaflets.

An artificial heart valve is a one-way valve implanted into a patient's heart to replace a malfunctioning natural heart valve. Birth defects, age, and effects of diseases can damage heart valves and necessitate artificial heart valve insertion. The most common types of artificial heart valves are mechanical heart valves and bioprosthetic heart valves.

SUMMARY

We describe here artificial heart valves that include materials having a negative Poisson's ratio ("NPR materials") that can provide various advantages. For instance, an inner portion of a leaflet can include an NPR material that can reduce a weight of the artificial heart valve and provide improved stress response characteristics, increasing the durability of the leaflet, e.g., to reduce a likelihood of damage to the leaflet compared to positive Poisson's ratio (PPR)-only heart valves. In some implementations, the use of the NPR material improves performance of the heart valve over time, such as by reducing leakage through the valve when the valve is in a closed configuration and/or by reducing a pressure gradient through the heart valve when the heart valve is in an open configuration. In some implementations, a combination of an NPR inner leaflet body and a PPR outer leaflet body enclosing the NPR inner leaflet body provides a synergistic effect, e.g., because the PPR outer leaflet body can be a hard, durable, non-porous, and/or biocompatible material and the NPR inner leaflet body can be a less dense material with beneficial stress-response properties.

In one aspect, this disclosure describes artificial heart valves. In some implementations, an artificial heart valve includes a frame, one or more struts attached to the frame, and a leaflet configured to open and close a fluid flow path through the frame by moving in response to heartbeats. Movement of the leaflet is restricted by the one or more struts. The leaflet includes an inner leaflet body having a negative Poisson's ratio, and an outer leaflet body at least partially surrounding the inner leaflet body, the outer leaflet body having a positive Poisson's ratio.

In various implementations, the artificial heart valve can have any one or more of at least the following characteristics.

In some implementations, the outer leaflet body fully encloses the inner leaflet body.

In some implementations, the inner leaflet body includes a metal having the negative Poisson's ratio, the metal including at least one of stainless steel or titanium.

In some implementations, the inner leaflet body includes a carbon structure having the negative Poisson ratio. In some implementations, the carbon structure includes at least one of porous graphite, carbon nanotubes, activated carbon, carbon fibers, or a carbon lattice structure.

In some implementations, the inner leaflet body includes a polymer having the negative Poisson's ratio.

In some implementations, the outer leaflet body includes at least one of a non-porous polymer, a metal, or pyrolytic carbon.

In some implementations, the one or more struts include a first strut arranged on a first side of the leaflet, and a second strut arranged on a second side of the leaflet. The first strut and the second strut confine the leaflet between the first strut and the second strut.

In some implementations, the leaflet defines an aperture in the leaflet, and the one or more struts include a strut extending through the aperture.

In some implementations, the leaflet is a first leaflet and the artificial heart valve includes a second leaflet. The one or more struts include a first strut about which the first leaflet is configured to pivot, and a second strut about which the second leaflet is configured to pivot, such that the fluid flow path is opened between the first leaflet and the second leaflet as the first leaflet and the second leaflet pivot in opposite directions.

Another aspect of this disclosure describes methods of making an artificial heart valve. In some implementations, according to the method, an inner leaflet body is formed including a precursor material. A stimulus is applied to the precursor material, the stimulus causing the precursor material to have a negative Poisson's ratio. An outer leaflet body is formed at least partially surrounding the inner leaflet body, to form a leaflet including the inner leaflet body and the outer leaflet body, the outer leaflet body having a positive Poisson's ratio. The leaflet is arranged with respect to one or more struts of the artificial heart valve such that movement of the leaflet opens and closes a fluid flow path through the artificial heart valve, the one or more struts restricting movement of the leaflet.

Implementations of the method can have any one or more of at least the following characteristics.

In some implementations, the outer leaflet body fully encloses the inner leaflet body.

In some implementations, the stimulus includes at least one of heat or pressure.

In some implementations, the precursor material comprises a porous foam. In some implementations, the porous foam includes at least one of a porous metal foam or a porous carbon foam.

In some implementations, the one or more struts include a first strut arranged on a first side of the leaflet, and a second strut arranged on a second side of the leaflet. The first strut and the second strut confine the leaflet between the first strut and the second strut.

In some implementations, the method includes forming an aperture in the leaflet. The one or more struts include a strut extending through the aperture.

In some implementations, the leaflet is a first leaflet, and the artificial heart valve includes a second leaflet. The one or more struts include a first strut about which the first leaflet is configured to pivot, and a second strut about which the second leaflet is configured to pivot, such that the fluid flow path is opened between the first leaflet and the second leaflet as the first leaflet and the second leaflet pivot in opposite directions.

Other implementations are also within the scope of the claims.

DETAILED DESCRIPTION

We describe here artificial heart valves that include materials having a negative Poisson's ratio ("NPR materials"), sometimes referred to as auxetic materials. In particular, in some implementations, a leaflet of an artificial heart valve includes an inner leaflet body and an outer leaflet body, where the inner leaflet body is formed of one or more NPR materials and the outer leaflet body is formed of one or more materials having positive Poisson's ratios (PPR materials). For example, the outer leaflet body can enclose the inner leaflet body. This composition can facilitate reduced weight and improved stress response characteristics over time.

Figure 1:
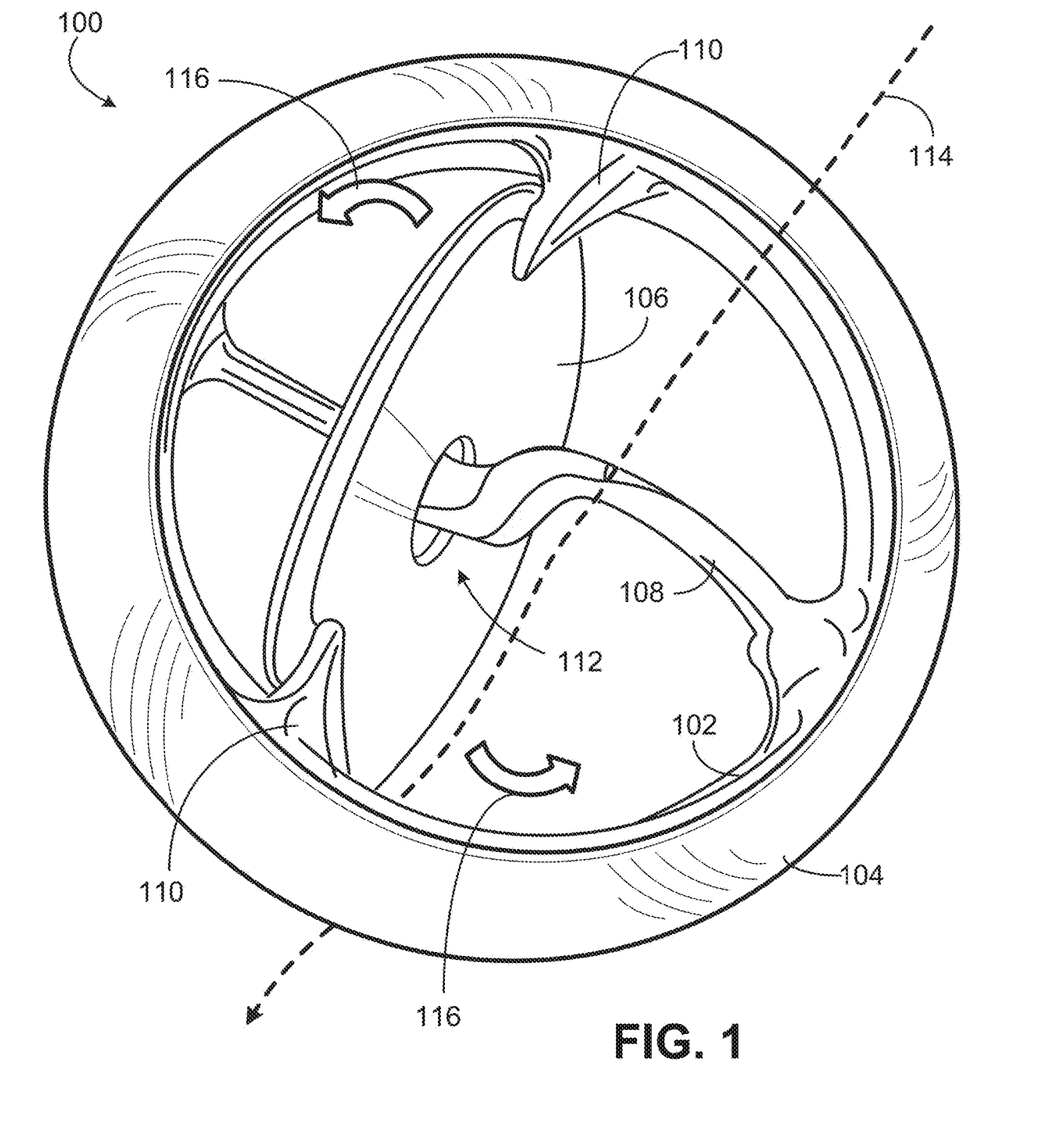
FIG. 1 is a diagram illustrating an example artificial heart valve.

Referring to FIG. 1, an example artificial heart valve 100 (which we sometimes refer to merely as a "heart valve") is shown. The heart valve 100 includes a frame 102, in this example having a ring shape. Other shapes of the frame 102, such as oval-shaped or polygon-shaped, can instead be implemented, depending on a location and orientation in which the heart valve 100 is to be placed in a patient's heart. Sizes of the heart valve 100 can also vary based on a type of the valve, a size of the heart of the patient, etc., but in some cases the heart valve 100 has a size (e.g., a largest dimension) between 19 mm and 33 mm.

In some implementations, the frame 102 (sometimes referred to as a "sewing ring") is formed at least partly of one or more metals, ceramics, and/or polymers. For example, in some implementations the frame 102 includes stainless steel, titanium, or another metal that includes one or both of those metals (e.g., an alloy of one or both of those metals). In some implementations, the frame 102 includes pyrolytic carbon, in either pure form or in combination with another material such as tungsten (used to increased visibility of the frame 102) and/or silicon (used to increase a hardness/strength of the frame 102). Pyrolytic carbon is useful as a material in heart valves because pyrolytic carbon has relatively low thrombogenicity compared to materials of comparable strength, hardness, and durability, meaning that blood in contact with pyrolytic carbon is relatively less likely to clot. Pyrolytic carbon also has sufficient strength, hardness, and durability to maintain its structural effectiveness over decades, as is desired for long-lasting artificial heart valves. In some implementations, the frame 102 includes graphite, e.g., graphite coated in pyrolytic carbon. In some implementations, the frame 102 includes one or more polymers, such as polyurethane and/or polyether ether ketone (e.g., polyurethane coated in polyether ether ketone). In some implementations, frame 102 includes a combination of these and/or other materials.

In some implementations, a fabric 104, such as a polymeric fabric (e.g., polyester), is mounted on the frame 102, e.g., sewn into the frame 102. The fabric 104 is sometimes referred to as a "sewing cuff" or "suture ring." During installation of the heart valve 100, the fabric 104 is sewn into surrounding tissue of the patient, and ingrown tissue eventually renders the valve-tissue fixation viable.

The heart valve 100 also includes a movable leaflet 106 (a "disc") and a guide structure that limits movement of the leaflet 106. The leaflet 106 and the guide structure are configured and arranged so that changing pressures on two sides of the heart valve 100 (e.g., blood pressures driven by heartbeats) alternately open and close the heart valve 100 through movement of the leaflet 106. In this example, the guide structure includes a primary strut 108 and two secondary struts 110, each strut 108, 110 attached to the frame 102. The primary strut 108 passes through an aperture 112 in the leaflet 106 (e.g., at a center of the leaflet 106). In the example configuration of FIG. 1, the leaflet 106 is in an "open" position, having rotated until being restricted by the secondary struts 110. Blood is therefore permitted to travel through the heart valve 100 through a fluid flow path 114. In response to a heartbeat-driven change in pressure, the leaflet 106 rotates in direction 116 until contacting a blocking portion of the primary strut 108, and the leaflet 106 comes to rest blocking the fluid flow path 114 in a "closed" position.

"Struts," as used herein, refers any structure that mechanically restricts movement of a leaflet, e.g., nubs, posts, axles, rails, shafts, and studs. These structures in an artificial heart valve are collectively referred to as a "guide structure."

Various properties of the heart valve 100 determine its effectiveness. In some cases, an effective heart valve 100 exhibits low regurgitation, meaning a low volume of blood leaking backwards through the heart valve 100 when it is closed (e.g., less than 5 mL per heartbeat). Low regurgitation can be provided by a tight (low-leakage) seal between the leaflet 106 and the frame 102 when the leaflet 106 is in the closed position. In some cases, an effective heart valve 100 exhibits a low transvalvular pressure gradient, meaning that a pressure drop in blood flowing through the heart valve 100 when the leaflet 106 is in the open position is small (e.g., less than 20 mm Hg). Low transvalvular pressure gradient can be provided by a hydrodynamic arrangement of the leaflet 106, guide structure, and frame 102 when the leaflet 106 is in the open position. In some cases, an effective heart valve 100 has low thrombogenicity, to reduce the likelihood of blood clotting at the heart valve 100.

The guide structure (in this example, the primary strut 108 and secondary struts 110) can be formed of any of the materials described above in reference to the frame 102. In some implementations, the guide structure is formed at least partially from pyrolytic carbon (e.g., is fully pyrolytic carbon and/or coated in pyrolytic carbon). This can help the guide structure maintain its durability as it is repeatedly struck by the rotating leaflet 106.

Figure 2:
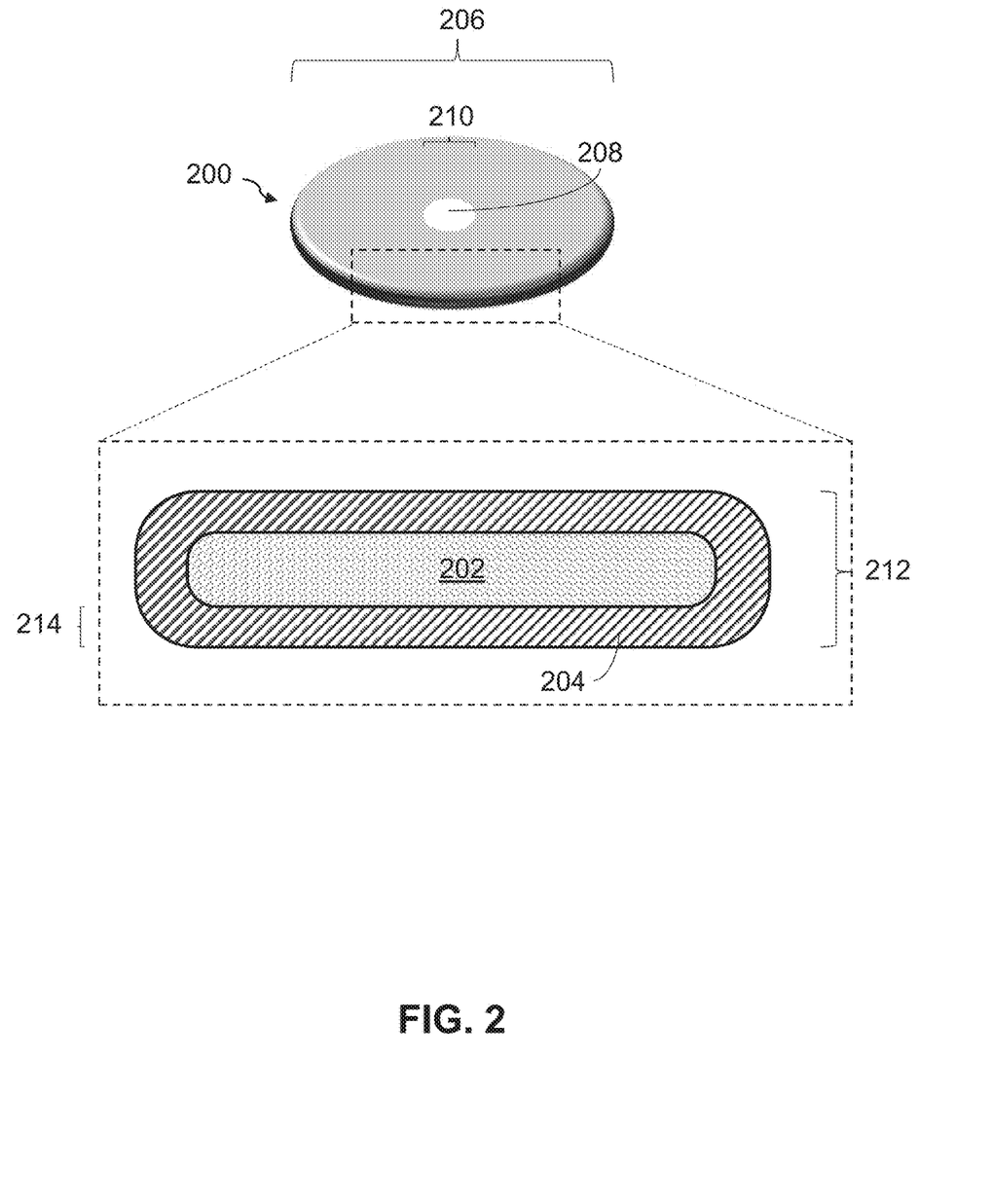
FIG. 2 is a diagram illustrating an example leaflet.

In some implementations, as shown in FIG. 2, a heart valve disc 200 (e.g., the leaflet 106) includes NPR material. In this example, one or more NPR materials form an inner leaflet body 202 that is enclosed by an outer leaflet body 204 formed of one or more PPR materials. In some implementations, as shown here, the outer leaflet body 204 fully encloses/coats the inner leaflet body. In some implementations, at least some portion of the inner leaflet body 202 is not covered by the outer leaflet body 204; for example, in some implementations, a portion of the inner leaflet body 202 that does not contact the guide structure is exposed. Both the inner leaflet body 202 and the outer leaflet body 204 can be annularly-shaped around an aperture 208, such that the inner leaflet body 202 is fully enclosed by the outer leaflet body 204 even at the aperture 208.

The combination of the NPR inner leaflet body 202 and the PPR outer leaflet body 204 can, in some implementations, combine useful characteristics of both NPR and PPR materials in a synergistic fashion. As described in more detail below, the NPR inner leaflet body 202 can provide reduced weight and improved stress response characteristics that can improve durability, performance, and/or longevity of the heart valve. However, some NPR materials are porous (e.g., porous to blood), which can lead to blood clotting, poor hydrodynamic characteristics, and/or poor sealing in a closed leaflet position. Moreover, some NPR materials have low hardness and accordingly might be damaged by repeated contact with other portions of the heart valve. The PPR outer leaflet body 204 can be non-porous and have a high hardness so as to wholly or partially mitigate these potential drawbacks of NPR material inclusion. In addition, a material of the PPR outer leaflet body 204 can be selected for biocompatibility (e.g., low thrombogenicity, non-toxicity, and/or unlikeliness to promote an adverse immune response), while a material of the NPR inner leaflet body 202, which does not contact tissue directly, can be selected to provide other benefits such as reduced weight and structural/stress-response benefits, as described in more detail below, even if the material of the NPR inner leaflet body 202 is, in some implementations, less biocompatible.

External and internal dimensions of the disc 200 (not shown to scale) can vary depending on the implementation. In some implementations, the disc has a diameter 206 between 18 mm and 32 mm, such as between 20 mm and 30 mm. In some implementations, the aperture 208 of the disc 200 has a diameter 210 between 1 mm and 5 mm, such as 3 mm. In some implementations, the disc 200 has a thickness 212 between 0.5 mm and 3 mm or between 0.5 mm and 2 mm, such as 1 mm. In some implementations, a thickness 214 of the outer leaflet body 204 is between 0.1 mm and 2 mm or between 0.1 mm and 1 mm, such as 0.25 mm. In some implementations, the thickness 214 of the outer leaflet body 204 is between 1% and 25% of the total thickness 212 of the disc 200. Other values for these dimensions are also within the scope of this disclosure. In some implementations, the leaflet is not a disc but, rather, is a semicircle or another shape, e.g., a shape configured to provide improved hydrodynamic characteristics.

An NPR material is a material that has a Poisson's ratio that is less than zero, such that when the material experiences a positive strain along one axis (e.g., when the material is stretched), the strain in the material along the two perpendicular axes is also positive (e.g., the material expands in cross-section). Conversely, when the material experiences a negative strain along one axis (e.g., when the material is compressed), the strain in the material along a perpendicular axis is also negative (e.g., the material compresses along the perpendicular axis). By contrast, a material with a PPR material has a Poisson's ratio that is greater than zero. When a PPR material experiences a positive strain along one axis (e.g., when the material is stretched), the strain in the material along the two perpendicular axes is negative (e.g., the material compresses in cross-section), and vice versa.

Figure 3:
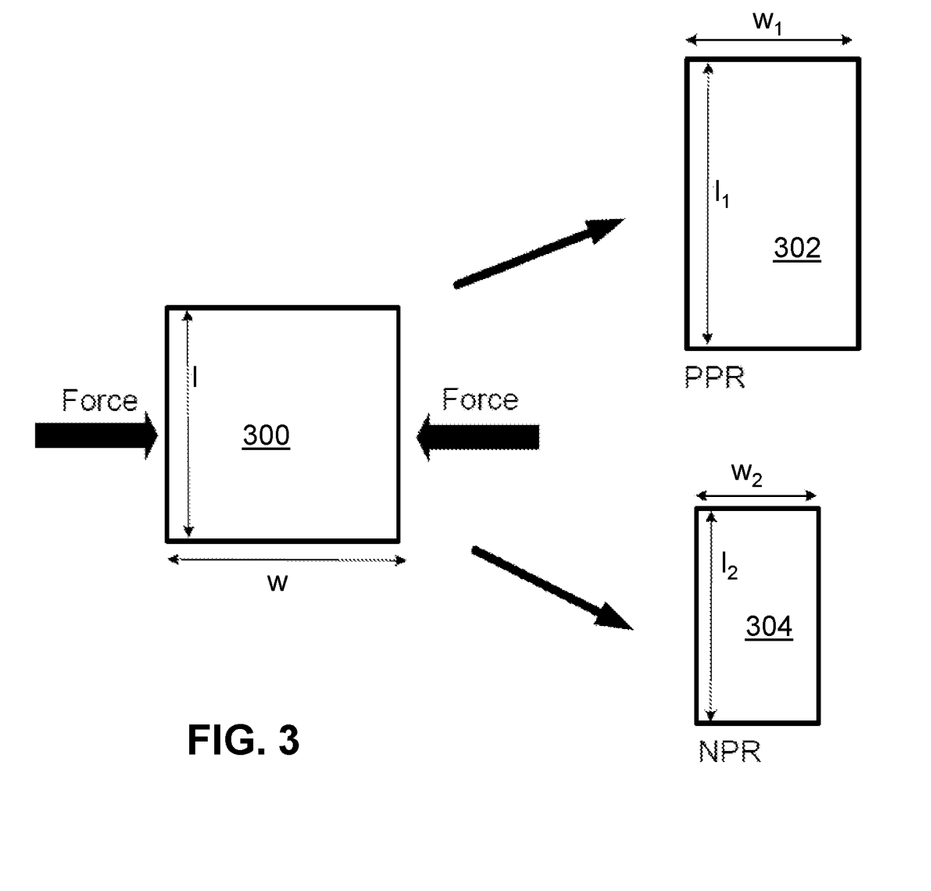
FIG. 3 is a diagram illustrating example materials with negative and positive Poisson's ratios.
Figure 4A:
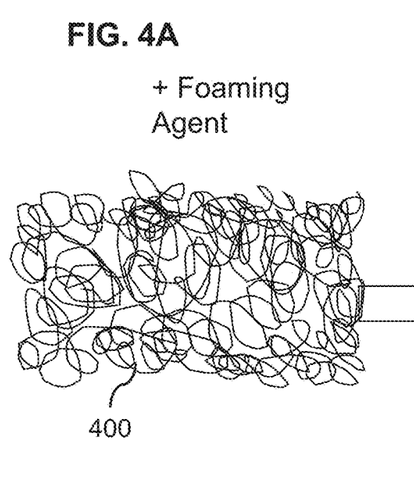
FIGS. 4A-4E are diagrams illustrating an example method of making a leaflet of an artificial heart valve.
Figure 4B:
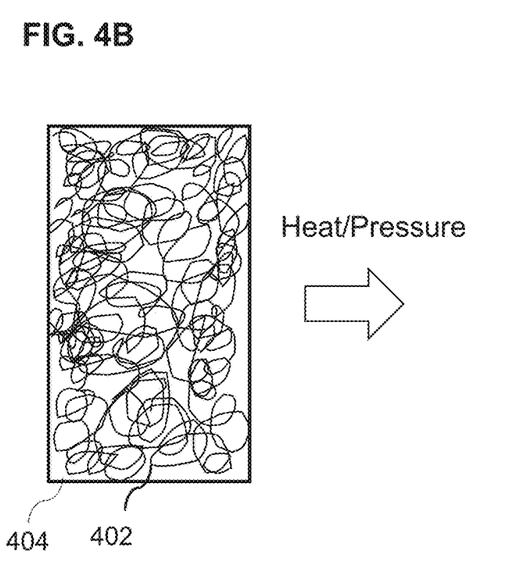
Figure 4C:
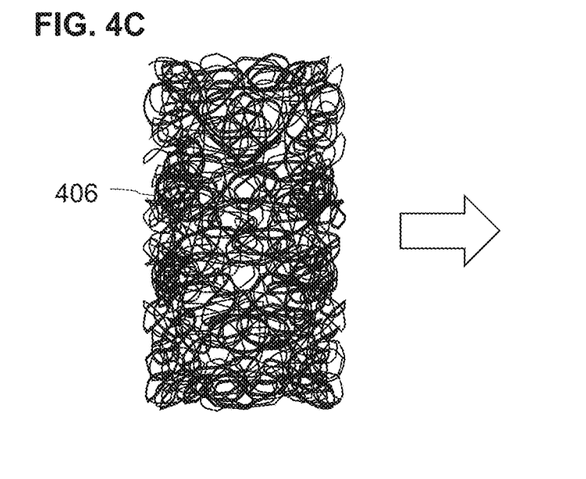
Figure 4D:
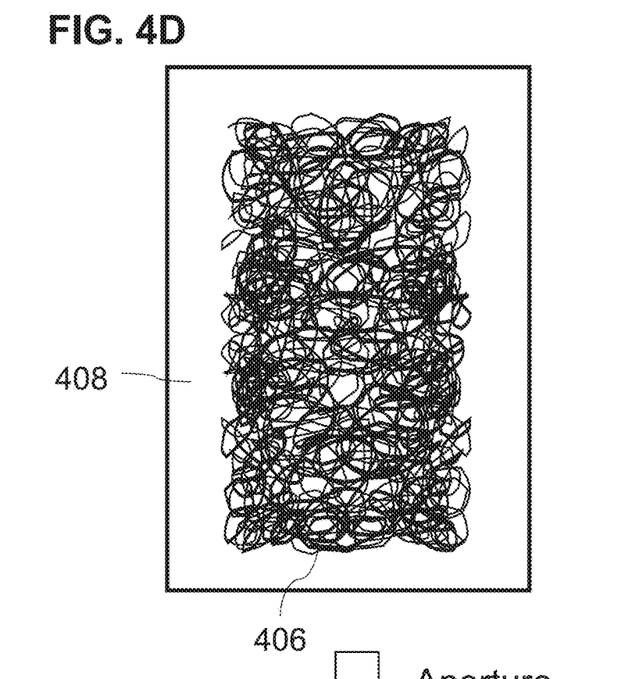
Figure 4E:
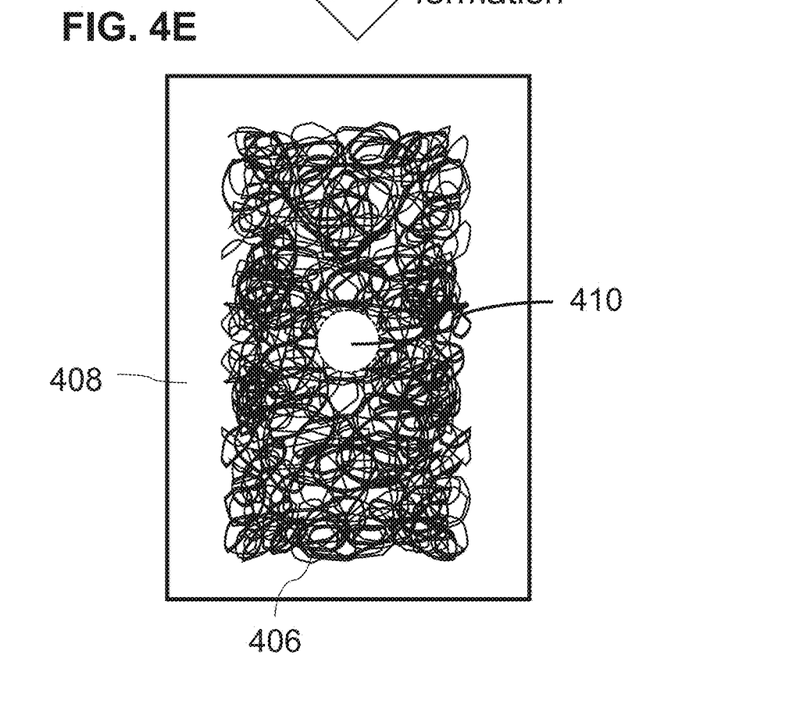

Materials with negative and positive Poisson's ratios are illustrated in FIG. 3, which depicts a hypothetical two-dimensional block of material 300 with length l and width w.

If the hypothetical block of material 300 is a PPR material, when the block of material 300 is compressed along its width w, the material deforms into the shape shown as block 302. The width w1 of block 302 is less than the width w of block 300, and the length l1 of block 302 is greater than the length l of block 300: the material compresses along its width and expands along its length.

By contrast, if the hypothetical block of material 300 is an NPR material, when the block of material 300 is compressed along its width w, the material deforms into the shape shown as block 304. Both the width w2 and the length l2 of block 304 are less than the width w and length l, respectively, of block 300: the material compresses along both its width and its length.

NPR materials for integration into artificial heart valve leaflets can be foams, such as polymeric foams, ceramic foams, metallic foams, carbon foams, or combinations thereof. A foam is a multi-phase composite material in which one phase is gaseous and the one or more other phases are solid (e.g., polymeric, ceramic (e.g., a carbon-based ceramic), metallic, otherwise carbon-based, or a combination thereof). Foams can be closed-cell foams, in which each gaseous cell is sealed by solid material; open-cell foams, in which each cell communicates with the outside atmosphere; or mixed, in which some cells are closed and some cells are open.

An example of an NPR foam structure is a re-entrant structure, which is a foam in which the walls of the cells are concave, e.g., protruding inwards toward the interior of the cells. In a re-entrant foam, compression applied to opposing walls of a cell will cause the four other, inwardly directed walls of the cell to buckle inward further, causing the material in cross-section to compress, such that a compression occurs in all directions. Similarly, tension applied to opposing walls of a cell will cause the four other, inwardly directed walls of the cell to unfold, causing the material in cross-section to expand, such that expansion occurs in all directions. NPR foams can have a Poisson's ratio of between −1 and 0, e.g., between −0.8 and 0, e.g., −0.8, −0.7, −0.6, −0.5, −0.4, −0.3, −0.2, or −0.1. NPR foams can have an isotropic Poisson's ratio (e.g., Poisson's ratio is the same in all directions) or an anisotropic Poisson's ratio (e.g., Poisson's ratio when the foam is strained in one direction differs from Poisson's ratio when the foam is strained in a different direction).

An NPR foam can be polydisperse (e.g., the cells of the foam are not all of the same size) and disordered (e.g., the cells of the foam are randomly arranged, as opposed to being arranged in a regular lattice). An NPR foam can have a characteristic dimension (e.g., the size of a representative cell, such as the width of the cell from one wall to the opposing wall) ranging from 0.1 μm to about 3 mm, e.g., about 0.1 μm, about 0.5 μm, about 1 μm, about 10 μm, about 50 μm, about 100 μm, about 500 μm, about 1 mm, about 2 mm, or about 3 mm.

Examples of polymeric foams for integration into leaflets include thermoplastic polymer foams (e.g., polyester polyurethane or polyether polyurethane); viscoelastic elastomer foams; or thermosetting polymer foams such as silicone rubber. Examples of metallic foams include metallic foams based on steel (e.g., stainless steel), copper, aluminum, titanium (e.g., $Ti_6Al_4V$, TiNbZr, or unalloyed titanium), or other metals, or alloys thereof, or ceramics composed of a metal oxide (e.g., aluminum oxide, titanium oxide, or zirconium oxide).

In some implementations, a carbon-based material can have a negative Poisson's ratio. Examples of carbon-based materials that can exhibit negative Poisson's ratio for stresses in at least some directions include porous graphite, bulk carbon nanotubes, activated carbon, collections of carbon fibers (e.g., porous carbon fibers and/or other carbon fibers), and certain carbon lattice structures (e.g., three-dimensional carbon honeycomb structures and/or fullerenes). In some implementations, a carbon-based structure is combined with one or more polymers (e.g., resin), e.g., as a carbon-fiber-reinforced polymer (CFRP) structure. In some implementations, the use of a carbon-based material for the inner leaflet body can be particularly advantageous when the outer leaflet body is also carbon-based, e.g., pyrolytic carbon, because strong carbon-carbon bonds can form between the inner leaflet body and the outer leaflet body. Additional details on some example carbon-based materials that can have negative Poisson's ratio (and/or that can be used as PPR materials in alternative states) can be found in Section 6.7, "Carbons," of *Biomaterials: An Introduction* (Springer, $3^{rd}$ edition) by Joon Park and R. S. Lakes, the section being incorporated herein by reference in its entirety. Additional details can also be found in Section 10.4, "Diamond-Like Carbon (DLC) Coatings," of *Bioceramics* (Springer) by Joon Park, the section being incorporated herein by reference in its entirety.

NPR-PPR composite materials are composites that include both regions of NPR material and regions of PPR material. NPR-PPR composite materials can be laminar composites, matrix composites (e.g., metal matrix composites, polymer matrix composites, or ceramic matrix composites), particulate reinforced composites, fiber reinforced composites, or other types of composite materials. In some examples, the NPR material is the matrix phase of the composite and the PPR material is the reinforcement phase, e.g., the particulate phase or fiber phase. In some examples, the PPR material is the matrix phase of the composite and the NPR material is the reinforcement phase.

Artificial heart valve leaflets that incorporate NPR materials can provide various benefits. First, because NPR materials are often less dense than counterpart PPR materials made of the same underlying compounds (e.g., NPR stainless steel may be less dense than PPR stainless steel), leaflets that include at least some NPR material can be lighter than PPR-only leaflets. This can reduce stress imposed by the valve on the heart and on valve-heart fixations such as the fabric 104. Over the long term, the reduced weight can result in improved stability of the valve, e.g., reduced probability of the valve becoming dislodged.

Second, because NPR materials compress along a first axis in response to compression along a second axis orthogonal to the first axis, leaflets that include NPR materials can be less likely to expand and (i) damage a portion of the leaflet itself and/or (ii) compromise another portion of the heart valve, such as struts. Stresses on the leaflet can be caused, for example, by movement of the leaflet itself (e.g., the leaflet striking struts of the heart valve), by differential blood pressures on the leaflet, and/or by long-term changes in heart size or heart state that put pressure on the artificial heart valve. With respect to the leaflet itself, expansion of the inner leaflet body can cause cracking and/or shedding of a coating of the leaflet (e.g., a pyrolytic outer leaflet body), compromising hemocompatibility of the leaflet (e.g., low thrombogenicity of the leaflet). With respect to other portion (s) of the heart valve, expansion of the leaflet has the potential to compromise the regurgitation properties of the heart valve, by preventing an effective leaflet seal from being formed; to compromise the transvalvular pressure gradient of the heart valve, by modifying an open position and/or orientation of the leaflet into a less hydrodynamic position and/or orientation; and/or to cause physical damage to other portions of the heart valve, such as struts of the heart valve, by causing additional and/or undesired contact between the leaflet and the other portions.

Referring again to FIG. 2, the inner leaflet body 202 includes one or more NPR materials, e.g., one or more of the NPR materials described above. In some implementations, the inner leaflet body 202 is entirely formed of one or more NPR materials. In some implementations, the inner leaflet body includes an NPR-PPR composite material. The outer leaflet body 204 has a positive Poisson's ratio. In some implementations, the outer leaflet body 204 includes one or more materials described in reference to the frame 102, e.g., a stainless steel and/or titanium-including metal, a polymer such as polyurethane, and/or pyrolytic carbon (e.g., silicon- and/or tungsten-including pyrolytic carbon). In some implementations, the inner leaflet body 202 and the outer leaflet body 204 include, respectively, NPR and PPR structures formed of the same element or compound. For example, in some implementations the inner leaflet body 202 includes an NPR porous carbon structure, and the outer leaflet body 204 includes pyrolytic carbon. This can provide higher-strength bonds between the inner leaflet body 202 and the outer leaflet body 204, and/or can provide improved thermal characteristics due to more similar thermomechanical responses between the inner leaflet body 202 and the outer leaflet body 204. Note that leaflets according to this disclosure need not include a PPR material but can, in some implementations, be entirely formed of any one or more of the NPR materials described herein.

NPR portions of heart valve leaflets, such as the inner leaflet body 202 of FIG. 2, can be produced in a variety of ways. In some implementations, an initially PPR material (sometimes referred to as a "precursor material") is converted into the NPR material. For example, a porous PPR sponge or foam can be transformed to change its structure into a structure that exhibits a negative Poisson's ratio. In some examples, NPR foams are produced by transformation of nanostructured or microstructured PPR materials, such as nanospheres, microspheres, nanotubes, microtubes, or other nano- or micro-structured materials, into a foam structure that exhibits a negative Poisson's ratio. The transformation of a PPR foam or a nanostructured or microstructured material into an NPR foam can involve thermal treatment (e.g., heating, cooling, or both), application of pressure, or a combination thereof. In some examples, PPR materials, such as PPR foams or nanostructured or microstructured PPR materials, are transformed into NPR materials by chemical processes, e.g., by using glue. In some examples, NPR materials are fabricated using micromachining or lithographic techniques, e.g., by laser micromachining or lithographic patterning of thin layers of material. In some examples, NPR materials are fabricated by additive manufacturing (e.g., three-dimensional (3D) printing) techniques, such as stereolithography, selective laser sintering, or other appropriate additive manufacturing technique.

In an example, a PPR thermoplastic foam, such as an elastomeric silicone film, can be transformed into an NPR foam by compressing the PPR foam, heating the compressed foam to a temperature above its softening point, and cooling the compressed foam. In an example, a PPR foam composed of a ductile metal can be transformed into an NPR foam by uniaxially compressing the PPR foam until the foam yields, followed by uniaxial compression in other directions.

FIGS. 4A-4E illustrate an example method of making a heart valve leaflet, such as the disc 200, leaflet 602, or leaflet 706, having an internal NPR portion. A granular or powdered material 400, such as a polymer material (e.g., a rubber), a metal (e.g., stainless steel, titanium, or an alloy thereof), or carbon, is mixed with a foaming agent to form a porous material (e.g., a sponge or a foam) 402. The porous material 402 is placed into a mold 404. Pressure is applied to compress the porous material 402, and the compressed porous material 402 is heated to a temperature above its softening point. The compressed, heated porous material 402 is then allowed to cool, resulting in an NPR material 406 (e.g., the internal leaflet body 202) produced from the initially-PPR porous material 402. The NPR material 406 is covered with an outer PPR material 408 (e.g., the outer leaflet body 204), which is adhered to the NPR material 406. In some implementations, heat and pressure applied again to cure and/or bond together the NPR material 406 and the PPR material 408 to form a cohesive structure. In the case of a leaflet defining an aperture, the aperture 410 can be formed (e.g., drilled) in the NPR material 406 before covering with the outer PPR material, or the aperture can be formed after covering with the outer PPR material.

Figure 5A:
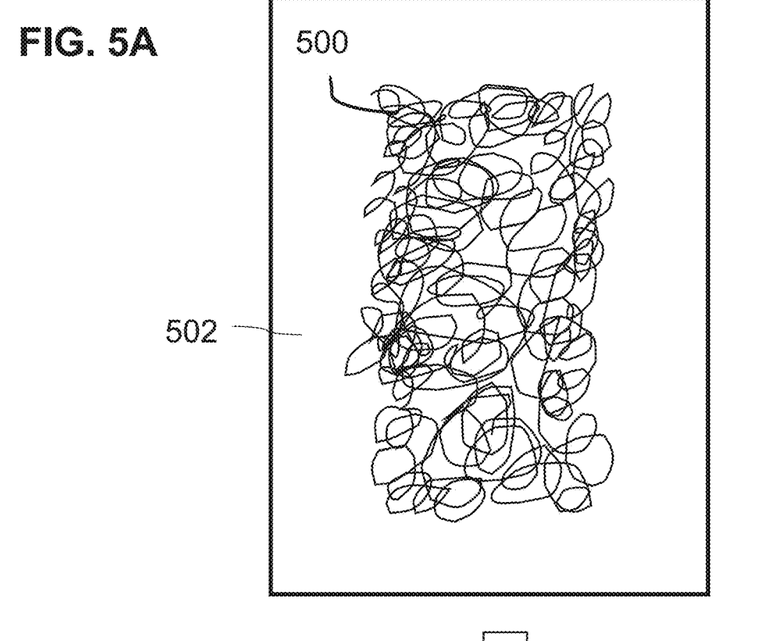
FIGS. 5A-5B are diagrams illustrating an example method of making a leaflet of an artificial heart valve.

FIGS. 5A-5B show an example of another method of fabricating a leaflet with an internal NPR portion, such as disc 200, leaflet 602, or leaflet 706. As shown in FIG. 5A, a precursor material 500 is enclosed in a PPR material 502. In some implementations, the precursor material 500 and the PPR material 502 are adhered and/or bonded together.

Figure 5B:
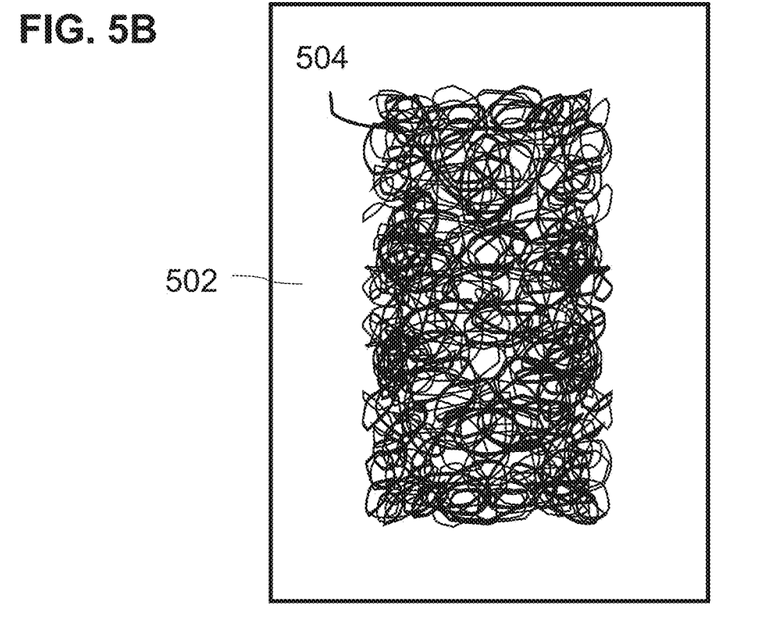

Heat and/or pressure are applied to convert the precursor material 500 into an NPR portion 504 enclosed in the PPR material 502. In some implementations, the heat and/or pressure that convert the precursor material 500 into the NPR portion 504 concurrently cure and/or bond together the NPR portion 504 and the PPR material 502, reducing fabrication complexity and cost. In some implementations, the PPR material 502 is itself modified by the heat and/or pressure, e.g., to convert a first form of carbon into a second form of carbon (e.g., into pyrolytic carbon).

Figure 6:
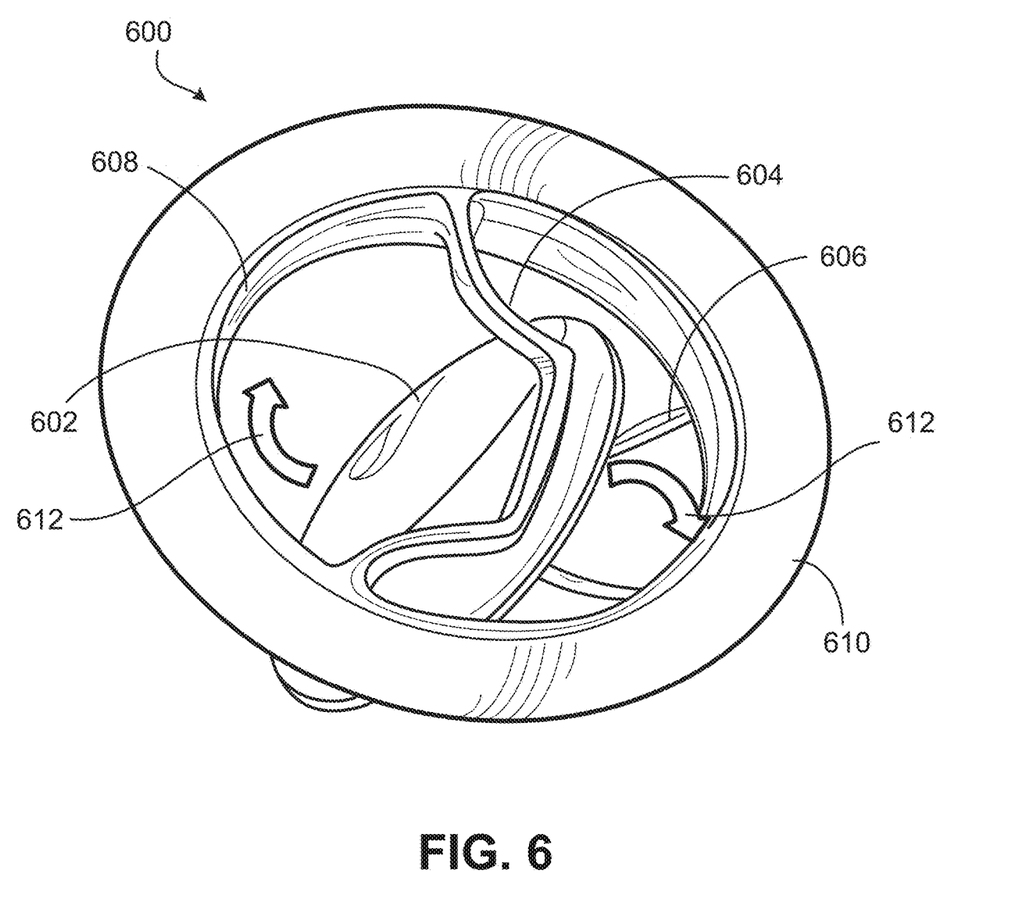
FIG. 6 is a diagram illustrating an example artificial heart valve.
Figure 7:
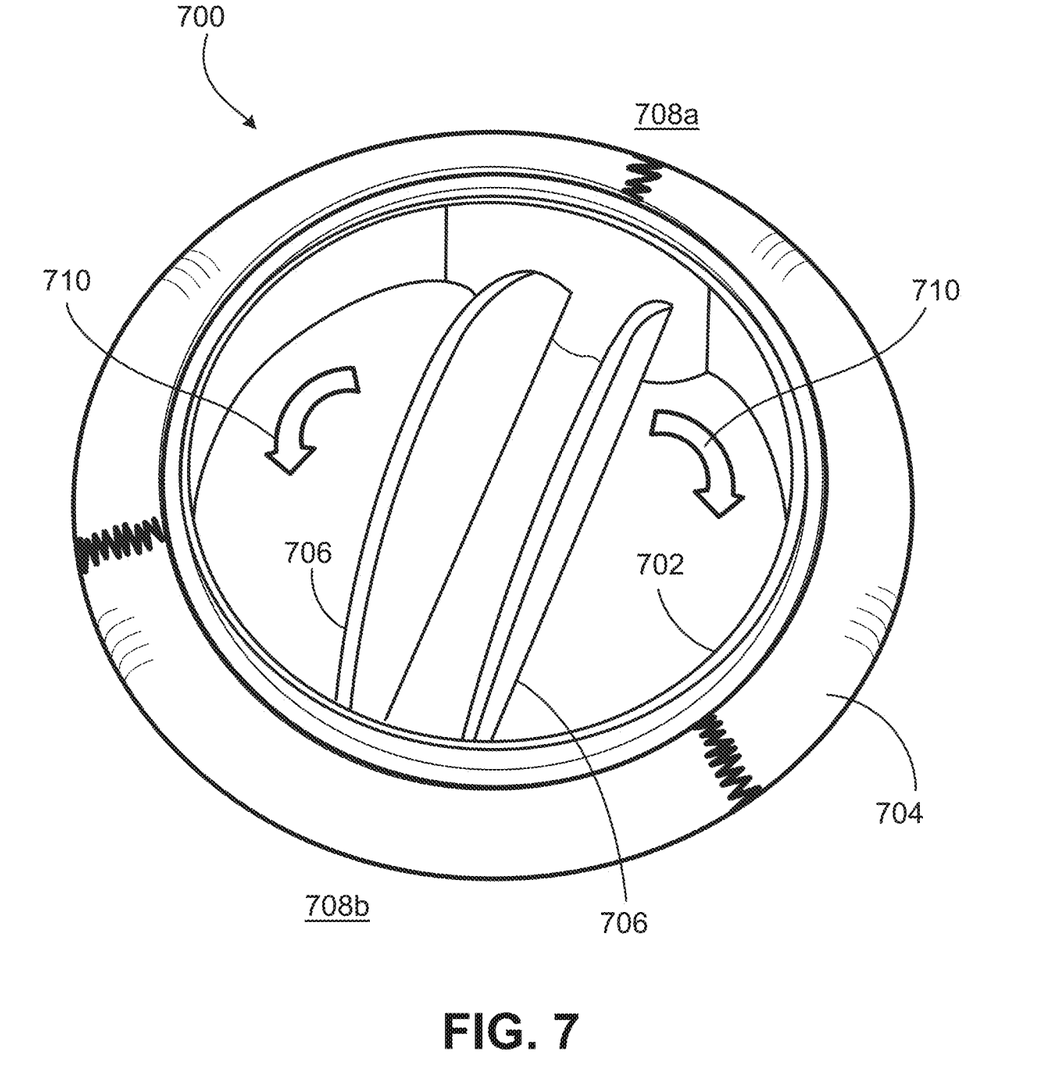
FIG. 7 is a diagram illustrating an example artificial heart valve.

After a leaflet has been fabricated (e.g., as shown in FIG. 4A-4E or 5A-5B), the leaflet can be arranged in an artificial heart valve as shown in FIGS. 1, 6, and 7. For example, in some implementations other portions of the artificial heart valve (e.g., a guide structure and frame) are formed, arranged, and/or attached together around the leaflet such that movement of the leaflet is restricted by the guide structure.

The example heart valve 100 is a mechanical monoleaflet valve and, more specifically, is a Medtronic Hall valve, characterized by its single leaflet having a strut passing through an aperture therein. Other mechanical valve designs are also within the scope of this disclosure, as described in several examples below. Additional details on mechanical valves and leaflets can be found in Section 10.4, "Heart Valve Implants," of *Biomaterials: An Introduction* (Springer, 3rd edition) by Joon Park and R. S. Lakes, the section being incorporated herein by reference in its entirety.

FIG. 6 shows a monoleaflet Bjork-Shiley artificial heart valve 600 incorporating a leaflet 602 including an NPR material. The leaflet 602 is a disc. In some implementations, the leaflet 602 includes an NPR inner leaflet body and a PPR outer leaflet body as described in reference to heart valve disc 200, and the leaflet 602 can have any or all of the characteristics described in reference to the heart valve disc 200, such as dimensions, materials, and methods of manufacture.

Instead of being mounted on a primary strut through an aperture as described for leaflet 106, the leaflet 602 is arranged in-between an inlet strut 604 on a first side of the leaflet 602 and an outlet strut 606 on a second side of the leaflet 602, the two struts 604, 606 together attached to a frame 608 and forming a guide structure. The inlet strut 604 and outlet strut 606 define a range of motion for the leaflet 602 such that the leaflet alternately opens/closes against the frame 608 of the heart valve 600 in response to heartbeats. From the open position shown in FIG. 6, the leaflet 602 rotates in direction 612 to close. Fabric 610 secures the heart valve 600 to a patient's heart. Characteristics of components of the heart valve 600 can be the same as described for corresponding components of the heart valve 100, unless indicated otherwise.

FIG. 7 shows a bileaflet artificial heart valve 700 (a "St. Jude" valve). In some cases, bileaflet valves can provide improved blood flow (e.g., a reduced transvalvular pressure gradient) compared to otherwise-similar monoleaflet valves. The heart valve 700 includes a frame 702 supporting fabric 704, each of which can have characteristics as described for frame 102 and fabric 104. As a bileaflet valve, the heart valve 700 also includes two approximately semicircular leaflets 706, shown in FIG. 7 in an open position. Each leaflet 706 rotates around a respective strut (not shown) extending along a chord of the frame from side 708a to side 708b. The struts extend through extended apertures in the leaflets 706. In response to heartbeats that alter pressures across the heart valve 700, the leaflets 706 rotate in respective opposite directions 710 to become flush with the 702 and also fit together along the leaflets' substantially straight edges, in a closed position that blocks blood flow through the heart valve 700.

In some implementations, each leaflet 706 includes an NPR inner leaflet body and a PPR outer leaflet body as described in reference to heart valve disc 200. Dimensions, materials, and methods of manufacture of the leaflet 706 can be as described for disc 200. Characteristics of components of the heart valve 700 can be the same as described for corresponding components of the heart valve 100, unless indicated otherwise.

In some implementations, a heart valve includes more than two leaflets, e.g., in a design similar to the Triflo trileaflet valve. Each of the three or more leaflets can include an NPR material, e.g., include an NPR inner leaflet body enclosed in a PPR outer leaflet body.

Figure 8:
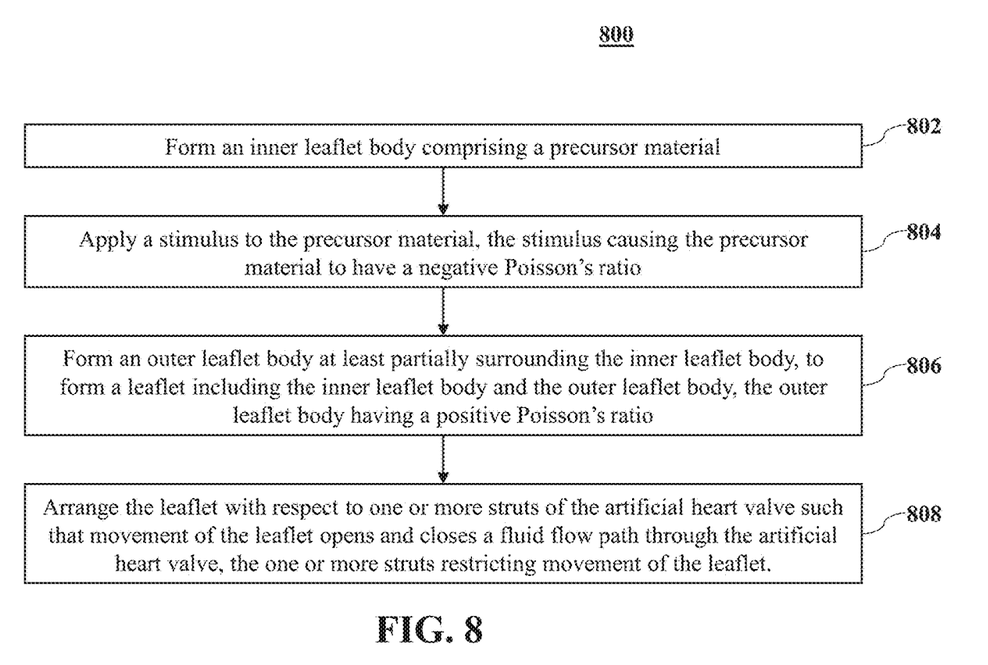
FIG. 8 is a diagram illustrating an example method of making an artificial heart valve.

FIG. 8 shows an example process 800 in accordance with this disclosure. An inner leaflet body is formed including a precursor material (802). A stimulus is applied to the precursor material, the stimulus causing the precursor material to have a negative Poisson's ratio (804). For example, the inner leaflet body with the negative Poisson's ratio can be inner leaflet body 202. An outer leaflet body is formed at least partially surrounding the inner leaflet body (e.g., fully enclosing the inner leaflet body), to form a leaflet including the inner leaflet body and the outer leaflet body, the outer leaflet body having a positive Poisson's ratio (806). The leaflet is arranged with respect to a guide structure of the artificial heart valve such that movement of the leaflet opens and closes a fluid flow path through the artificial heart valve, the guide structure restricting movement of the leaflet (808). For example, the artificial heart valve can be heart valve 100, 600, or 700.

Various modifications will be apparent from the foregoing detailed description. For example, shapes and dimensions (both absolute and relative) can be modified without departing from the scope of this disclosure. The example artificial heart valve structures described (e.g., positions, forms, arrangements, and number of struts; shapes and arrangements of leaflets) are exemplary; other structures/designs can be used instead or additionally. Further, features described above in connection with different implementations may, in some cases, be combined in the same implementation. In some instances, the order of the process steps may differ from that described in the particular examples above.

Accordingly, other implementations are also within the scope of the claims.

What is claimed is:

1. An artificial heart valve comprising:
   a frame;
   one or more struts attached to the frame; and
   a leaflet configured to open and close a fluid flow path through the frame by moving in response to heartbeats, wherein movement of the leaflet is restricted by the one or more struts, and
   wherein the leaflet comprises
      an inner leaflet body having a negative Poisson's ratio, wherein the inner leaflet body comprises a carbon structure having the negative Poisson ratio, and
      an outer leaflet body at least partially surrounding the inner leaflet body, the outer leaflet body having a positive Poisson's ratio.

2. The artificial heart valve, of claim 1, wherein the outer leaflet body fully encloses the inner leaflet body.

3. The artificial heart valve of claim 1, wherein the carbon structure comprises at least one of porous graphite, carbon nanotubes, activated carbon, carbon fibers, or a carbon lattice structure.

4. The artificial heart valve of claim 1, wherein the outer leaflet body comprises at least one of a non-porous polymer, a metal, or pyrolytic carbon.

5. The artificial heart valve of claim 1, wherein the one or more struts comprise:
   a first strut arranged on a first side of the leaflet; and
   a second strut arranged on a second side of the leaflet,
   wherein the first strut and the second strut confine the leaflet between the first strut and the second strut.

6. The artificial heart valve of claim 1, wherein the leaflet defines an aperture in the leaflet, and
   wherein the one or more struts comprise a strut extending through the aperture.

7. The artificial heart valve of claim 1, wherein the leaflet is a first leaflet,
   wherein the artificial heart valve comprises a second leaflet, and
   wherein the one or more struts comprise
      a first strut about which the first leaflet is configured to pivot, and
      a second strut about which the second leaflet is configured to pivot,
   such that the fluid flow path is opened between the first leaflet and the second leaflet as the first leaflet and the second leaflet pivot in opposite directions.

8. A method of making an artificial heart valve, the method comprising:
   forming an inner leaflet body comprising a precursor material;
   applying a stimulus to the precursor material, the stimulus causing the precursor material to have a negative Poisson's ratio;
   forming an outer leaflet body at least partially surrounding the inner leaflet body, to form a leaflet comprising the inner leaflet body and the outer leaflet body, the outer leaflet body having a positive Poisson's ratio, wherein the inner leaflet body comprises a carbon structure having the negative Poisson ratio; and
   arranging the leaflet with respect to one or more struts of the artificial heart valve, the struts attached to a frame, such that movement of the leaflet opens and closes a fluid flow path through the frame in response to heartbeats, the one or more struts restricting movement of the leaflet.

9. The method of claim 8, wherein the outer leaflet body fully encloses the inner leaflet body.

10. The method of claim 8, wherein the stimulus comprises at least one of heat or pressure.

11. The method of claim 8, wherein the precursor material comprises a porous foam.

12. The method of claim 11, wherein the porous foam comprises at a porous carbon foam.

13. The method of claim 8, wherein the one or more struts comprise:
   a first strut arranged on a first side of the leaflet; and
   a second strut arranged on a second side of the leaflet,
   wherein the first strut and the second strut confine the leaflet between the first strut and the second strut.

14. The method of claim 8, comprising:
   forming an aperture in the leaflet,
   wherein the one or more struts comprises a strut extending through the aperture.

15. The method of claim 8, wherein the leaflet is a first leaflet,
   wherein the artificial heart valve comprises a second leaflet, and
   wherein the one or more struts comprise
      a first strut about which the first leaflet is configured to pivot, and
      a second strut about which the second leaflet is configured to pivot,
   such that the fluid flow path is opened between the first leaflet and the second leaflet as the first leaflet and the second leaflet pivot in opposite directions.

* * * * *